United States Patent [19]
Arvidsson

[11] Patent Number: 6,082,705
[45] Date of Patent: Jul. 4, 2000

[54] MEMBRANE VALVE WHEREIN THE MEMBRANE IS DISPLACED BY A COMBINATION OF FLUID FLOW AND OPERATION OF A SOLENOID

[75] Inventor: Carl-Erik Arvidsson, Solna, Sweden

[73] Assignee: Siemens Elema AB, Solna, Sweden

[21] Appl. No.: 09/052,138

[22] Filed: Mar. 31, 1998

[30] Foreign Application Priority Data

Apr. 4, 1997 [SE] Sweden ................................ 9701240

[51] Int. Cl.[7] .................................................. F16K 31/02
[52] U.S. Cl. .............................. 251/129.07; 251/129.17; 251/331
[58] Field of Search ................... 251/129.07, 129.17, 251/331

[56] References Cited

U.S. PATENT DOCUMENTS 5,265,594  11/1993  Olsson et al. .

FOREIGN PATENT DOCUMENTS 0 354 123  2/1990  European Pat. Off. .
273 982   12/1989  Germany .

Primary Examiner—Kevin Shaver
Assistant Examiner—John P. Welsh
Attorney, Agent, or Firm—Hill & Simpson

[57] ABSTRACT

A valve for regulating the flow of a medium has a valve housing with an inlet for the medium that is to be regulated, and an outlet for a regulated medium flow, a valve face with a valve opening, a movable sealing part that is arranged so that it is influenced by the medium flow in the direction of opening of the valve, and which closes and opens the valve opening as well as regulating the flow of medium through the valve opening. The valve further has an arrangement for controlling the position of the sealing part. In order to obtain a valve of this type in which a gas flow can be regulated with a high degree of precision, and can seal hermetically in a closed position using simple and inexpensive structure, a duct for the flow of the medium is arranged between the inlet and the side of the movable sealing part facing away from the valve face.

2 Claims, 1 Drawing Sheet

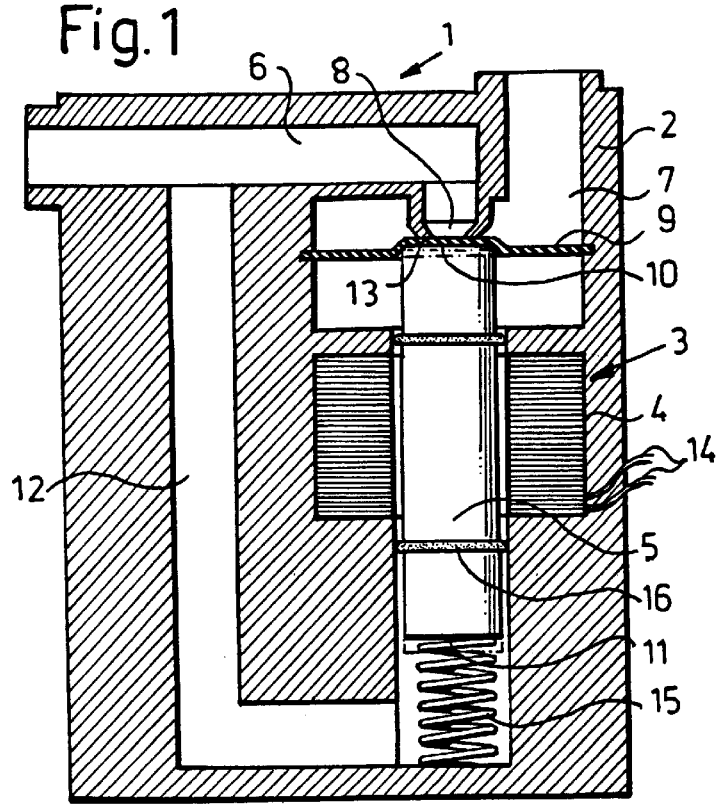
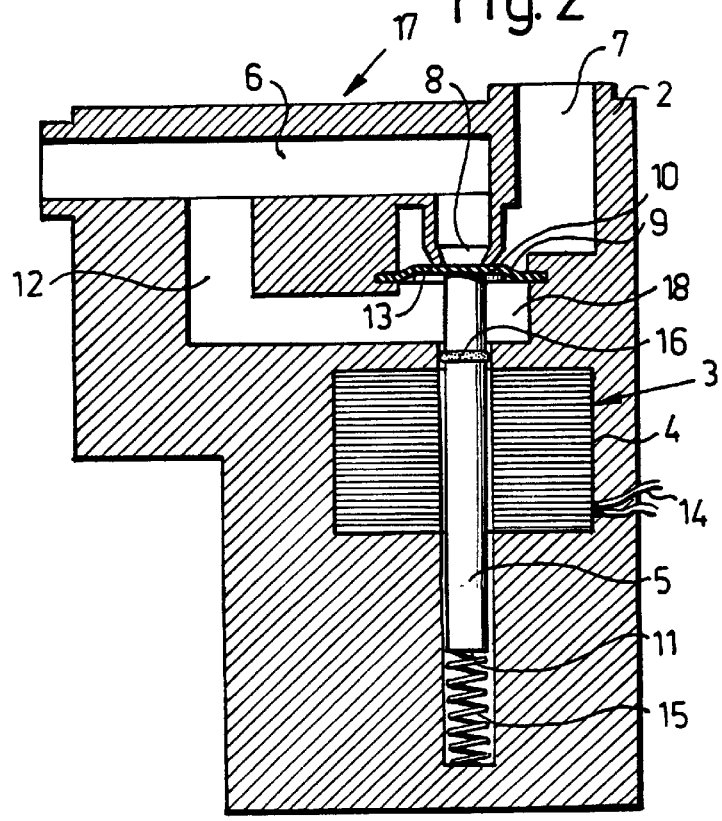

MEMBRANE VALVE WHEREIN THE MEMBRANE IS DISPLACED BY A COMBINATION OF FLUID FLOW AND OPERATION OF A SOLENOID

BACKGROUND OF THE INVENTION

1. Field of the Invention

The present invention relates to a valve for regulating the flow of a medium, of the type having a valve housing with an inlet for the medium that is to be regulated and an outlet for a regulated flow of the medium, a valve face with a valve opening, a movable sealing part which is arranged so that it is influenced by the flow of medium in the direction of opening of the valve, and that closes and opens the valve opening as well as regulates the flow of medium through the valve opening, and means for controlling the position of the sealing part.

2. Description of the Prior Art

A valve of this type is known from U.S. Pat. No. 5,265,594. Particularly in connection with the supply of gas to a patient connected to a breathing apparatus, it is very important that the amount of gas be controlled with great precision with the aid of such a valve. It is also very important that the sealing part, which here consists of a solenoid and a membrane, hermetically seals the valve opening when the supply of current to the solenoid is shut off. In connection with the valve specified in the aforementioned patent, this is ensured because the shaft of the solenoid, which influences the membrane and on which no magnetic force operates any longer when the current is shut off, is influenced by a relatively powerful spring so as to press the membrane against the valve face. During the regulation of the gas flow, a powerful spring of this sort can inhibit the motions of the solenoid. A relatively powerful solenoid can of course solve this problem, however, such a solenoid is relatively large, and is therefore space-consuming and has a high current consumption.

SUMMARY OF THE INVENTION

An object of the present invention is to provide a valve of the type described above in which a gas flow can be regulated with great precision, and which, in a closed position, can seal hermetically using simple and thus inexpensive means.

This object is achieved according to the invention in a valve having a duct for the flow of medium arranged between the inlet and the side of the movable sealing part disposed facing from the valve face. When the valve opening seals in the way described above with the aid of the sealing part, the gas from the inlet, which has flowed into the inventively provided duct, presses against the aforementioned side of the sealing part, and thereby contributes to keeping the valve opening closed. In this way, a relatively small solenoid can be used for the opening and closing of the valve opening, as well as for regulating the gas through the valve opening. The spring which urges the membrane against the valve face need only be dimensioned so as to compensate the weight of the solenoid shaft, in contrast to the strong spring described above in the prior art valve.

In an embodiment of the valve according to the invention, the side of the sealing part facing away from the valve face has a larger surface area than that of the valve opening. By this means, it is further ensured that the sealing part seals hermetically in a sealing position against the valve face.

The sealing part can be a membrane that is clamped fixedly on the valve housing and a solenoid with a shaft, in which one end of the shaft is arranged to alter the position of the membrane. Either the other end of the shaft or the side of the membrane facing away from the valve represents the aforementioned larger-area side.

In East German Patent 273 982, a valve for regulating a gas flow is specified. The valve is provided with a membrane that opens or closes the valve opening with the aid of a gas, with the gas pressing more or less against the side of the membrane facing away from the valve face. The gas pressure against the membrane is relatively large, and thus the membrane can lift off from the valve face only when the gas pressure on the membrane decreases. The membrane is thus provided with a hole that goes through it, which serves to bleed a part of the gas that presses against the membrane, and to let it into the space of the valve opening. The hole in the membrane is opened or closed with the aid of a solenoid. Accordingly, the solenoid does not control the movements of the membrane, but rather is provided only in order to bring about the aforementioned pressure compensation. Due to the fact that gas flows into the valve opening, partly through the hole in the membrane and partly due to the fact that the membrane lifts off from the valve face, a high degree of precision in the controlling of the gas flow through the valve is not achieved.

DESCRIPTION OF THE DRAWINGS

FIG. 1 is a side sectional view of a first embodiment of a valve constructed in accordance with the principles of the present invention.

FIG. 2 is a side sectional view of a second embodiment of a valve constructed in accordance with the principles of the present invention.

DESCRIPTION OF THE PREFERRED EMBODIMENTS

FIG. 1 shows, partly in section, an embodiment of a valve according to the invention. The valve has a valve housing 2 and a solenoid 3, including a solenoid housing 4 and a shaft 5, the solenoid 3 being embodied (fixed) in the valve housing 2. The valve housing 2 has a flow-through duct for a flow of medium that is to be regulated, whereby the duct is divided into an inlet 6, an outlet 7, and a valve opening 8 arranged in between. A membrane 9 is attached precisely in front of the valve opening 8. The membrane 9 is held fixedly in the valve housing 2, and, with one end face 10 of the solenoid shaft 5 which regulates the position of the membrane 9, the flow of medium is also regulated. The medium may be, e.g. a gas, to a patient, in connection with a respirator (not shown). In this exemplary embodiment, a duct 12 for the flow of medium, filled with gas from the inlet 6, is arranged between the inlet 6 and the second end face 11 of the solenoid shaft 5. FIG. 1 shows that the end face 10 of the shaft 5 of the solenoid 3 lies against the membrane 9 in a closed valve position, in which the membrane 9 presses against the valve face 13 of the valve opening 8. In order to obtain an open valve position, shown with dotted contours of the membrane 9 and the shaft 5 more or less current is supplied to the solenoid 3 via lines 14, influencing the-haft 5 in such a way that it is drawn into the solenoid housing 4, i.e. downwardly in FIG. 1, so that the membrane 9 lifts off as desired from the valve face 13 due to the resilience of the material and due to the gas pressure on the inlet side, so that gas can flow to the patient via the valve opening 8 and via the outlet 7. When the current supply to the solenoid 3 is shut off, a magnetic force no longer operates on this shaft 5, and with the aid of a pressure spring 15, the shaft 5 presses the membrane 9 against the valve face 13 in such a way that the valve opening is sealed. In this sealed position of the valve opening 8, the gas from the medium flow duct 12 presses against the end side 11 of the solenoid shaft 5, and contributes to pressing the shaft 5 and the membrane 9 against the valve face 13. By dimensioning the surface area of the medium flow duct 12 on the end face 11 of the shaft 5 so that it is larger than the surface size of the valve opening 8, an extraordinarily good seal is obtained. The shaft 5 is provided with at least one seal 16, which prevents gas from penetrating into the solenoid 3, which could otherwise destroy the solenoid 3.

FIG. 2 shows a further embodiment of a valve 17 according to the invention, which is very similar to the valve 1 according to FIG. 1, and which operates as described in connection with this FIG. 1. The difference is that in the embodiment of FIG. 2 the medium flow duct 12 extends from the inlet 6 to a space 18 connected to the membrane 9. In this exemplary embodiment, the end face 10 of the solenoid shaft 5 is also constructed as a flange. When the shaft 5 presses the membrane 9 against the valve face 13 with the aid of the pressure spring 15, so that the valve opening 8 is sealed, the gas from the medium flow duct 12 presses directly against the flange-shaped end side of the shaft 5, and against the free surfaces of the membrane 9.

The surface size of the mentioned parts against which the gas in the space 18 presses is greater than the surface size of the valve opening 8. This means that an extremely good seal of the valve opening 8 is given.

In both the exemplary embodiments, only one spring is required, which is dimensioned such that it compensates the weight of the solenoid shaft 5. By means of this relatively soft spring, only a relatively weak, small, inexpensive and current-saving solenoid is required for the regulation of the gas flow.

With the invention, simple and therefore inexpensive means are used to achieve a safety feature sought in this connection, namely that in case of power failure the valve is hermetically sealed, and an unmonitored or uncontrolled emission of gas to the patient is prevented.

Although modifications and changes may be suggested by those skilled in the art, it is the intention of the inventor to embody within the patent warranted hereon all changes and modifications as reasonably and properly come within the scope of his contribution to the art.

I claim as my invention:

1. A valve for regulating a flow of a medium comprising:
    a valve housing having an inlet for incoming medium to be regulated, and, an outlet from which regulated medium flows, said inlet and said outlet defining a regulated flow path therebetween;
    a valve face having a valve opening disposed in said housing between said inlet and said outlet;
    a membrane disposed adjacent said valve opening having an edge region fixedly held in said valve housing and having a membrane region which is movable by said medium in said regulated flow path in a direction of flow of said medium in a direction which opens said valve opening;
    a duct in said housing through which said medium flows in addition to flowing in said regulated flow path, disposed between said inlet and a side of said membrane region facing away from said valve face; and
    an energizable solenoid having a solenoid shaft, said solenoid shaft having a first end adjacent said membrane region and causing displacement of said membrane region dependent on energization of said solenoid, and said solenoid shaft having an opposite second end disposed for communicating with said medium in said duct, said medium in said duct acting on said solenoid shaft in combination with energization of said solenoid to displace said membrane region.

2. A valve as claimed in claim 1 wherein said side of said membrane region facing away from said valve face has a larger surface area than said valve opening.

* * * * *